United States Patent [19]

Cohen

[11] Patent Number: 4,973,596

[45] Date of Patent: Nov. 27, 1990

[54] METHOD OF ADMINISTERING A NARCOTIC ANALGESIC AND DOSAGE FORMS THEREFOR

[75] Inventor: Edwin A. Cohen, Mahwah, N.J.

[73] Assignee: Barr Laboratories, Inc., Pomona, N.Y.

[21] Appl. No.: 196,658

[22] Filed: May 20, 1988

[51] Int. Cl.$^5$ .............................................. A61K 31/44
[52] U.S. Cl. ................................................... 514/354
[58] Field of Search ......................................... 514/354

[56] References Cited

U.S. PATENT DOCUMENTS

| | | | |
|---|---|---|---|
| 3,921,636 | 11/1975 | Zaffaroni | 128/260 |
| 3,948,254 | 4/1976 | Zaffaroni | 128/127 |
| 3,948,262 | 4/1976 | Zaffaroni | 128/260 |
| 3,967,618 | 7/1976 | Zaffaroni | 128/130 |
| 3,993,073 | 11/1976 | Zaffaroni | 128/260 |
| 4,014,987 | 3/1977 | Heller et al. | 424/15 |
| 4,180,064 | 12/1979 | Heller et al. | 128/130 |
| 4,226,848 | 10/1980 | Nagai et al. | 514/420 |
| 4,249,531 | 2/1981 | Heller et al. | 128/260 |
| 4,464,378 | 8/1984 | Hussain | 514/282 |
| 4,673,679 | 6/1987 | Aungst et al. | 514/282 |

*Primary Examiner*—Stanley J. Friedman
*Attorney, Agent, or Firm*—Cohen, Pontani & Lieberman

[57] ABSTRACT

The invention provides a novel method of administering meperidine or its pharmaceutically acceptable salts and novel dosage forms containing these compounds which are adapted for nasal administration. The nasal dosage forms disclosed include solutions, suspensions, gels and ointments.

24 Claims, No Drawings

METHOD OF ADMINISTERING A NARCOTIC ANALGESIC AND DOSAGE FORMS THEREFOR

FIELD OF THE INVENTION

The present invention relates to a method for the nasal administration of narcotic analgesics, namely, merperidine and its pharmaceutically acceptable salts. The invention also relates to nasal dosage forms of meperidine and its pharmaceutically acceptable salts.

BACKGROUND OF THE INVENTION

Meperidine hydrochloride is a potent narcotic analgesic with multiple actions qualitatively similar to those of morphine. The principal actions of therapeutic value are analgesia and sedation.

A 60 mg. to 80 mg. parenteral dose of meperidine hydrochloride is approximately equivalent in analgesic effect to 10 mg. of morphine. The onset of action is slightly more rapid than with morphine, and the duration of action is slightly shorter.

Heretofore, meperidine hydrochloride has been administered both by the oral route and the parenteral (subcutaneous, intramuscular and intravenous) route. However, according to the 1988 Physician's Desk Reference, page 2226, meperidine is significantly less effective by the oral than by the parenteral route, but the exact ratio of oral to parenteral effectiveness is unknown.

U.S. Pat. No. 4,464,378 teaches that morphine and pharmacologically active analogs thereof having at least one aromatic ring, said ring bearing at least one OH group and which are not well absorbed orally, can be delivered via nasal administration and greatly enhance the bioavailability as compared to the oral route.

U.S. Pat. No. 4,464,378 also discloses dosage forms adapted for nasal administration which comprise solutions, suspensions and gels containing a major amount of water in addition to the active ingredient. According to U.S. Pat. No. 4,464,378, nasal dosage forms are preferably isotonic.

However, U.S. Pat. No. 4,464,378 does not disclose or suggest that meperidine and/or its pharmaceutically acceptable salts can be delivered via nasal administration. Additionally, there is no teaching or suggestion that meperidine and/or its pharmaceutically acceptable salts when delivered via nasal administration would have enhanced bioavailability as compared to the oral route.

Some of the major hazards associated with meperidine, as with other narcotic analgesics, are respiratory depression and, to a lesser degree, circulatory depression, respiratory arrest, shock, and cardiac arrest. As such, care must be taken to administer the correct dose of meperidine and to avoid overdosage.

The usual dosage of meperidine for relief of pain is 50 mg. to 150 mg. intramuscularly, subcutaneously or orally, every 3 or 4 hours as necessary. However, as noted above, meperidine is less effective by the oral route than the parenteral route.

SUMMARY OF THE INVENTION

In view of the foregoing, it is apparent that a serious need exists for the improved delivery of meperidine and its pharmaceutically acceptable salts. Thus, it is an object of the invention to provide a method for administering meperidine and its pharmaceutically acceptable salts which avoids the use of a needle, as in parenteral administration.

It is also an object of the invention to provide a dosage form of meperidine and/or its pharmaceutically acceptable salts preferably containing a single predetermined dose so that accurate dosing can be achieved and the incidence of hazardous side effects reduced.

In accordance with the present invention, these and other objects are achieved by nasal administration of meperidine and/or its pharmaceutically acceptable salts in a pre-measured preferred single dose dosage form adapted for nasal administration.

DETAILED DESCRIPTION OF THE INVENTION

The invention provides a method of administering meperidine or one of its pharmaceutically acceptable salts to a warm blooded mammal in need of analgesia which overcomes the discomfort and inconvenience associated with parenteral administration. Additionally, the method according to the invention provides an alternative to oral administration which, in the case of meperidine hydrochloride, has been found to be significantly less effective than parenteral administration. The invention also provides pharmaceutical unit dosage forms of meperidine or one of its pharmaceutically acceptable salts which dosage form is suitable for nasal administration in the method according to the invention.

Meperidine is 1-methyl-4-phenyl-4-piperidinecarboxylic acid ethyl ester and has the following structural formula:

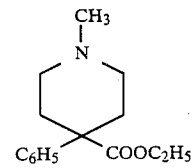

The synthesis of meperidine is well known and is disclosed for example in U.S. Pat. No. 2,167,351 which is incorporated herein by reference. A preferred pharmaceutically acceptable salt of meperidine is the hydrochloride salt thereof. Meperidine hydrochloride is marketed in the United States by Winthrop Pharmaceuticals, New York, New York, under the trademark DEMEROL.

According to the present invention, an analgesicly effective amount of meperidine or one of its pharmaceutically acceptable salts, particularly meperidine hydrochloride is nasally administered to a warm blooded mammal in need of analgesia. The analgesicly effective amount is in the range of about 25 to 150 mg., closer preferably to about 50 mg.

According to the present invention, the meperidine may be employed in its free acid form or in the form of a pharmaceutically acceptable salt thereof, such as, the hydrochloride salt. Suitable non-toxic pharmaceutically acceptable nasal carriers will be apparent to those skilled in the art of nasal pharmaceutical formulations. For those not skilled in the art, reference is made to the text entitled "Remington's Pharmaceutical Sciences", 14th Edition, 1970.

Obviously, the choice of suitable carriers will depend on the exact nature of the particular nasal dosage form desired, i.e., whether the drug is to be formulated into a nasal solution (for use as drops or as a spray), a nasal suspension, a nasal ointment or a nasal gel. Preferred nasal dosage forms are solutions, suspensions and gels, which contain a major amount of water (preferably purified water) in addition to the active ingredient. Minor amounts of other ingredients such as pH adjusters (e.g., a base such as NaOH), emulsifiers or dispersing agents, buffering agents, preservatives, wetting agents, gelling agents and viscosity modifiers (e.g., methyl cellulose) may also be present. Most preferably, as mentioned above, the nasal composition is isotonic, i.e. it has the same osmotic pressure as blood serum.

It is especially preferred that nasal administration be carried out using a single dose nasal administrator. Various single dose nasal administrators are commercially available. A particularly preferred single dose nasal administrator for use in accordance with the invention is a conically shaped single dose dispenser of one milliliter capacity referred to as a "1 ml. MAXIM" which may be obtained from CP Packaging Inc. 1075 Cranberry So. River Road, Dayton, New Jersey 08810.

It will be understood that volumes smaller than 1 ml. may be incorporated into the 1 ml. dispenser for single dose administration. Alternatively, dispensers having a maximum capacity smaller than 1 ml. may also be employed which, however, may be difficult to grasp between the fingers for squeezing the contents therefrom during nasal administration. Dispensers having maximum capacities greater than 1 ml. may also be employed, if desired.

It will also be understood that the dispenser should be manufactured from a material that is compatible with pharmaceuticals and is readily deformable, such materials being well-known in the art.

Additionally, it is not necessary in order to practice the method according to the invention, that the meperidine be administered using a single dose nasal administrator. Various pharmaceutical unit dosage forms for nasal administration of meperidine or its above-mentioned salts as the active compound in the method according to the invention may be employed. Preferably, the active compound is meperidine hydrochloride. Additionally, the pharmaceutical unit dosage forms according to the present invention may employ a pharmaceutically acceptable carrier, such as water and preferably isotonic saline. The active compound may be dissolved in the carrier or dispersed therein using suitable pharmaceutically acceptable dispersing agents as are known in the art. One preferred pharmaceutical unit dosage form according to the invention comprises a solution of meperidine hydrochloride in isotonic saline. It is especially preferred that the pH of the solution be adjusted to the range of about 3.5 to about 6. The pH of the solution may be adjusted, for example, using dilute sodium hydroxide or hydrochloric acid as required.

Preferably, the pharmaceutical unit dosage forms according to the present invention will contain an analgesicly effective amount of meperidine or its pharmaceutically acceptable salts in the range of about 25 to about 150 mg., most preferably about 50 mg. Additionally, it is preferred to use isotonic saline as a carrier in an amount of about 0.2 to about 2 ml, more preferably about 0.2 to about 1 ml. and most preferably about 0.5 to about 1 ml. For ease of administration and patient comfort, it is preferable that the volume of carrier material be kept small. Therefore, a most particularly preferred volume of isotonic saline is 0.5 ml.

Additionally, it is preferred that the pharmaceutical unit dosage forms according to the invention be sterile, although for nasal administration sterility is not required.

Thus, various types of unit dosage forms suitable for nasal administration may be employed. For example, the active compound can be formulated in suspensions, solutions or gels, the production of which would be within the ability of persons having ordinary skill in the art. However, as mentioned above, it is particularly preferred that the active compound be administered using a single dose nasal administrator as described hereinabove to facilitate the administration of precise dosages and thereby avoid undesirable side effects attributable to overdosage.

Some examples of the preparation of typical nasal compositions and unit dosage forms adapted for nasal administration are set forth below. However, it is to be understood that these examples are given by way of illustration only and are not to be construed as limiting the invention either in spirit or in scope as many modifications both in materials and in methods will be apparent to those skilled in the art.

EXAMPLE 1

5 g. meperidine hydrochloride can be dissolved in 80 ml. of distilled water and the pH of the resultant solution then adjusted to 6. A quantity of distilled water sufficient to bring the total volume to 100 ml. can then be added and sufficient sodium chloride (or other appropriate salt) added to adjust the solution to isotonicity. The solution can then be sterilized by known methods. The final solution would contain 25 mg. meperidine hydrochloride for 0.5 ml. of solution.

EXAMPLE 2

10 g. meperidine hydrochloride can be dissolved in 80 ml. of distilled water and the pH of the resultant solution then adjusted to 6. A quantity of distilled water sufficient to bring the total volume to 100 ml. can then be added and sufficient sodium chloride (or other appropriate salt) added to adjust the solution to isotonicity. The solution can then be sterilized by known methods. The final solution would contain 50 mg. meperidine hydrochloride per 0.5 ml. of solution.

EXAMPLE 3

7.5 g. meperidine hydrochloride can be dissolved in 80 ml. of distilled water and the pH of the resultant solution then adjusted to 6. The quantity of distilled water sufficient to bring the total volume to 100 ml. can then be added and sufficient sodium chloride (or other appropriate salt) added to adjust the solution to isotonicity. The solution can then be sterilized by known methods. The final solution will contain 75 mg. meperidine hydrochloride per 1.0 ml. of solution.

EXAMPLE 4

10 g. meperidine hydrochloride can be dissolved in 80 ml. of distilled water and the pH of the resultant solution then adjusted to 6. the quantity of the distilled water sufficient to bring the total volume to 100 ml, can then be added and sufficient sodium chloride (or other appropriate salt) added to adjust the solution to isotonicity. The solution can then be sterilized by known methods. Its final solution would contain 100 mg. meperidine hydrochloride per 1.0 ml. of solution.

EXAMPLE 5

A sterilized single dose nasal dispenser of 1 ml. maximum capacity can be filled with 0.5 ml. of the final solution prepared in Example 1. The dispenser can then be sealed. The resulting single dose nasal dosage form would contain 25 mg. meperidine hydrochloride in 0.5 ml. solution.

EXAMPLE 6

A sterilized single dose nasal dispenser of 1 ml. maximum capacity can be filled with 0.5 ml. of the final solution prepared in Example 2. The dispenser can then be sealed. The resulting single dose nasal dosage form would contain 50 mg. meperidine hydrochloride in 0.5 ml. solution.

EXAMPLE 7

A sterilized single dose nasal dispenser of 1 ml. maximum capacity can be filled with 1 ml. of the final solution prepared in Example 3. The dispenser can then be sealed. The resulting single dose nasal dosage form would contain 75 mg. meperidine hydrochloride in 1 ml. solution.

EXAMPLE 8

A sterilized single dose nasal dispenser of 1 ml. maximum capacity can be filled with 1 ml. of the final solution prepared in Example 4. The dispenser can then be sealed. The resulting single dose nasal dosage form would contain 100 mg. meperidine hydrochloride in 1 ml. of solution.

Naturally, the therapeutic dosage range for nasal administration of meperidine or its pharmaceutically acceptable salts according to the invention will vary with the size of the patient. Dosage may also need to be adjusted according to the severity of the pain and the response of the patient. Generally, the dosage for nasal administration will approximate the amounts previously employed for parenteral or oral administration. Thus, the usual dose for relief of pain will be in the range of about 25 mg. to 150 mg. The quantity of nasal dosage form needed to deliver the desired dose will of course depend on the concentration of drug in the nasal dosage form. For example, a dose of 50 mg. could be delivered in a single dose using a dosage form containing 50 mg. meperidine hydrochloride per 0.5 ml. solution. Alternatively, this same dose could be administered employing two applications of a dosage form containing 25 mg. meperidine hydrochloride in 0.5 ml. of solution.

While the invention has been described in terms of various preferred embodiments, the person having ordinary skill in the art will appreciate the various modifications, substitutions, omissions and additions that may be made without departing from the spirit thereof. Accordingly, it is intended that the scope of the present invention be limited solely by the scope of the following claims.

I claim:

1. A pharmaceutical unit dosage form for nasal administration to a warm blooded mammal in need of analgesia, said pharmaceutical unit dosage form comprising a nasal administration device which comprises an analgesicly effective amount of meperidine or a pharmaceutically acceptable salt thereof.

2. The pharmaceutical unit dosage form of claim 1, wherein the compound is meperidine hydrochloride.

3. The pharmaceutical unit dosage form of claim 2, wherein the nasal administration device further comprises a pharmaceutically acceptable carrier.

4. The pharmaceutical unit dosage form of claim 3, wherein the pharmaceutically acceptable carrier is sterile isotonic saline and the meperidine hydrochloride is dissolved in the isotonic saline to form a solution.

5. The pharmaceutical unit dosage form of claim 4, wherein the solution has a pH in the range of about 3.5 to about 6.

6. The pharmaceutical unit dosage form of claim 2, wherein the analgesicly effective amount of the meperidine hydrochloride is in the range of about 25 to about 150 mg.

7. The pharmaceutical unit dosage form of claim 6, wherein the analgesicly effective amount of the meperidine hydrochloride is about 50 mg.

8. The pharmaceutical unit dosage form of claim 6, wherein the nasal administration device further comprises isotonic saline as a carrier.

9. The pharmaceutical unit dosage form of claim 8, wherein the isotonic saline is present in an amount of about 0.2 to about 2 ml.

10. The pharmaceutical unit dosage form of claim 9, wherein the isotonic saline is present in an amount of about 0.2 to about 1 ml.

11. The pharmaceutical unit dosage form of claim 10, wherein the isotonic saline is present in an amount of about 0.5 to about 1 ml.

12. The pharmaceutical unit dosage form of claim 11, wherein the isotonic saline is present in an amount of about 0.5 ml.

13. The pharmaceutical unit dosage form of claim 7, wherein the nasal administration device further comprises isotonic saline solution.

14. The pharmaceutical unit dosage form of claim 13, wherein the isotonic saline solution is present in an amount of about 0.2 to about 2 ml.

15. The pharmaceutical unit dosage form of claim 14, wherein the isotonic saline solution is present in an amount of about 0.2 to about 1 ml.

16. The pharmaceutical unit dosage form of claim 15, wherein the isotonic saline is present in an amount of about 0.5 to about 1 ml.

17. The pharmaceutical unit dosage form of claim 16, wherein the isotonic saline is present in an amount of about 0.5 ml.

18. A pharmaceutical unit dosage form for nasal administration to a warm blooded mammal in need of analgesia, said pharmaceutical unit dosage form comprising a single dose nasal administration device which comprises a solution of 50 mg. meperidine hydrochloride in 0.5 ml. of isotonic saline and wherein the solution has a pH which is adjusted between about 3.5 to about 6.

19. A method for producing analgesia in a warm blooded mammal, which comprises nasally administering to the warm blooded mammal an analgesicly effective amount of meperidine or the pharmaceutically acceptable salts thereof.

20. The method according to claim 19, wherein the compound is meperidine hydrochloride.

21. The method according to claim 20, wherein the analgesicly effective amount is in the range of about 25 to about 150 mg.

22. The method according to claim 21, wherein the analgesicly effective amount is about 50 mg.

23. A method for producing analgesia in a warm blooded mammal in need of analgesia which comprises nasally administering to the warm blooded mammal a solution of about 50 mg. meperidine hydrochloride in about 0.5 ml. isotonic saline.

24. The method of claim 23, wherein the solution is nasally administered using a single dose nasal administration device.

* * * * *